US012788361B2

(12) United States Patent
Liu et al.

(10) Patent No.: US 12,788,361 B2
(45) Date of Patent: Nov. 10, 2026

(54) SYSTEMS AND METHODS FOR MEASURING BIOPHYSICAL ATTRIBUTES OF THE POSTERIOR EYE

(71) Applicant: OHIO STATE INNOVATION FOUNDATION, Columbus, OH (US)

(72) Inventors: Jun Liu, Columbus, OH (US); Sunny Kwok, Cincinnati, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 18/743,230

(22) Filed: Jun. 14, 2024

(65) Prior Publication Data

US 2024/0415488 A1 Dec. 19, 2024

Related U.S. Application Data

(60) Provisional application No. 63/472,978, filed on Jun. 14, 2023.

(51) Int. Cl.

*A61B 8/10* (2006.01)
*A61B 8/00* (2006.01)
*G06T 7/00* (2017.01)

(52) U.S. Cl.

CPC ................ *A61B 8/10* (2013.01); *A61B 8/485* (2013.01); *G06T 7/0014* (2013.01); *G06T 2207/10132* (2013.01); *G06T 2207/30041* (2013.01)

(58) Field of Classification Search

CPC .......... A61B 8/10; A61B 8/485; G06T 7/0014
See application file for complete search history.

(56) References Cited

U.S. PATENT DOCUMENTS

2015/0313573 A1* 11/2015 Liu .......................... A61B 3/16
600/398

OTHER PUBLICATIONS

Tang, Junhua. Ultrasonic characterization of corneal and scleral biomechanics. The Ohio State University, 2012.*
Pavlatos, Elias. Ultrasound Speckle Tracking Methods to Study the Biomechanical Factors of Ocular Disease. The Ohio State University, 2018.*
Lim, Shen Yi, et al. "Assessment of stiffness of posterior eye wall in myopic eyes with an ultrasound-based algorithm using strain elastography." Investigative Ophthalmology & Visual Science 63.7 (2022): 3815-3815.*
Silverman, Ronald H. "Principles of ophthalmic ultrasound." Expert review of ophthalmology 18.6 (2023): 379-389.*
Tham, Y.C., et al. Global prevalence of glaucoma and projections of glaucoma burden through 2040: a systematic review and meta-analysis. Ophthalmology 121, 2081-2090 (2014).
Bourne, R.R., et al. Number of People Blind or Visually Impaired by Glaucoma Worldwide and in World Regions 1990-2010: A Meta-Analysis. PLoS One 11, e0162229 (2016).

(Continued)

*Primary Examiner* — Carolyn A Pehlke
(74) *Attorney, Agent, or Firm* — Meunier Carlin & Curfman LLC

(57) ABSTRACT

A computer-implemented method for measuring biophysical properties of an eye. The computer-implemented method includes receiving ultrasound data and determining, preprocessing the ultrasound data to improve its signal-to-noise, and using ocular pulse elastography (OPE) to determine a measurement of a posterior portion of an eye of a subject based on the ultrasound data.

20 Claims, 3 Drawing Sheets

(56) References Cited

OTHER PUBLICATIONS

Rossetti, L., et al. Blindness and glaucoma: A multicenter data review from 7 academic eye clinics. PLoS ONE 10, 1-13 (2015).
Shaikh, Y., Yu, F. & Coleman, A.L. Burden of undetected and untreated glaucoma in the United States. American Journal of Ophthalmology 158, 1121-1129.e1121 (2014).
Peters, D., Bengtsson, B. & Heijl, A. Lifetime risk of blindness in open-angle glaucoma. American Journal of Ophthalmology 156, 724-730 (2013).
Holden, B.A., et al. Global Prevalence of Myopia and High Myopia and Temporal Trends from 2000 through 2050. Ophthalmology 123, 1036-1042 (2016).
Foster, P.J. & Jiang, Y. Epidemiology of myopia. Eye (Basingstoke) 28, 202-208 (2014).
Haarman, A.E.G., et al. The Complications of Myopia: A Review and Meta-Analysis. Invest Ophthalmol Vis Sci 61, 49 (2020).
Wang, X., et al. Peripapillary sclera exhibits a v-shaped configuration that is more pronounced in glaucoma eyes. Br J Ophthalmol 106, 491-496 (2022).
Wang, Y.X., et al. Peripapillary Scleral Bowing Increases with Age and Is Inversely Associated with Peripapillary Choroidal Thickness in Healthy Eyes. Am J Ophthalmol 217, 91-103 (2020).
Sigal, I.A., Flanagan, J.G. & Ethier, C.R. Factors Influencing Optic Nerve Head Biomechanics. Investigative Ophthalmology & Visual Science 46, 4189-4199 (2005).
Thornton, I.L., Dupps, W.J., Roy, A.S. & Krueger, R.R. Biomechanical effects of intraocular pressure elevation on optic nerve/lamina cribrosa before and after peripapillary scleral collagen cross-linking. Investigative Ophthalmology and Visual Science 50, 1227-1233 (2009).
Quigley, H.A., et al. Losartan treatment protects retinal ganglion cells and alters scleral remodeling in experimental glaucoma. PLoS ONE 10, 1-30 (2015).
Coudrillier, B., et al. Effects of peripapillary scleral stiffening on the deformation of the lamina cribrosa. Investigative ophthalmology & visual science 57, 2666-2677 (2016).
Grytz, R., Yang, H., Hua, Y., Samuels, B.C. & Sigal, I.A. Connective Tissue Remodeling in Myopia and its Potential Role in Increasing Risk of Glaucoma. Curr Opin Biomed Eng 15, 40-50 (2020).
McBrien, N.A., Cornell, L.M. & Gentle, A. Structural and ultrastructural changes to the sclera in a mammalian model of high myopia. Invest Ophthalmol Vis Sci 42, 2179-2187 (2001).
Harper, A.R. & Summers, J.A. The dynamic sclera: Extracellular matrix remodeling in normal ocular growth and myopia development. Experimental Eye Research 133, 100-111 (2015).
Ang, M., et al. Imaging in myopia: potential biomarkers, current challenges and future developments. Br J Ophthalmol 103, 855-862 (2019).
Boote, C., et al. Scleral structure and biomechanics. Prog Retin Eye Res 74, 100773 (2020).
Moriyama, M., et al. Quantitative analyses of high-resolution 3D MR images of highly myopic eyes to determine their shapes. Invest Ophthalmol Vis Sci 53, 4510-4518 (2012).
Ohno-Matsui, K., et al. Imaging retrobulbar subarachnoid space around optic nerve by swept-source optical coherence tomography in eyes with pathologic myopia. Investigative Ophthalmology & Visual Science 52, 9644-9650 (2011).
Clayson, Keyton, et al. “Ocular pulse elastography: imaging corneal biomechanical responses to simulated ocular pulse using ultrasound.” Translational Vision Science & Technology 9.1 (2020): 5-5.
Pavlatos, Elias, et al. “Imaging corneal biomechanical responses to ocular pulse using high-frequency ultrasound.” IEEE transactions on medical imaging 37.2 (2017): 663-670.

* cited by examiner

SYSTEMS AND METHODS FOR MEASURING BIOPHYSICAL ATTRIBUTES OF THE POSTERIOR EYE

CROSS-REFERENCE TO RELATED APPLICATION

This application claims priority to U.S. Provisional Patent Application No. 63/472,978, filed Jun. 14, 2023, entitled "SYSTEMS AND METHODS FOR MEASURING BIOPHYSICAL ATTRIBUTES OF THE POSTERIOR EYE," which is expressly incorporated herein by reference in its entirety.

STATEMENT REGARDING FEDERALLY FUNDED RESEARCH

This invention was made with government support under EY025358 awarded by the National Institutes of Health and EY032621 awarded by the National Institutes of Health. The government has certain rights in the invention.

BACKGROUND

The posterior eye can be defined as the structures behind the anterior hyaloid membrane of the eye. This can include the retina, choroid, sclera, and optic nerve, as well as the vitreous humor surrounding the retina. Diseases of the eye are common. For example, glaucoma is a leading cause of irreversible blindness worldwide and affects an estimated 3 million Americans. Although major advances in diagnosis and treatment have been made, glaucoma-related vision loss remains a significant public health problem. Myopia is another common cause of vision loss globally with an alarming rate of increase in prevalence. It is predicted that there will be approximately 4.8 billion people with myopia (about half of the world population) and approximately 1 billion with high myopia (about 10% of the total population) by 2050. High myopia increases the risk for pathologic ocular conditions such as glaucoma, retinal detachment, and myopic macular degeneration.

Current imaging technologies do not provide a satisfactory solution to measure characteristics of the posterior of the eye. For example, optical coherence tomography (OCT) has excellent resolution but small penetration depth and in general is limited to the retina and the anterior surface of the sclera. Magnetic Resonance Imaging (MRI) has been used to detect staphyloma in myopic eyes but is susceptible to unavoidable eye movements that blur the images leading to reduced accuracy.

The patient can be asked to hold their gaze for seconds and hundreds of ultrasound images with radiofrequency data are acquired for ultrasound speckle tracking analysis to obtain tissue displacements and strains.

Improvements to vision care strategies can reduce blindness caused by glaucoma and myopia, and the associated socioeconomical burden.

SUMMARY

Systems and methods for measuring the posterior eye are described herein.

In some aspects, the techniques described herein relate to a computer-implemented method for measuring biophysical properties of an eye, the computer-implemented method including: receiving ultrasound data; determining, using ocular pulse elastography (OPE), a measurement of a posterior portion of an eye of a subject based on the ultrasound data.

In some aspects, the techniques described herein relate to a computer-implemented method, wherein the ultrasound data includes high-frequency ultrasound data.

In some aspects, the techniques described herein relate to a computer-implemented method, wherein the high-frequency ultrasound data is about 20 MHz ultrasound data.

In some aspects, the techniques described herein relate to a computer-implemented method, wherein the ultrasound data includes an ultrasound cross section of the posterior portion of the eye.

In some aspects, the techniques described herein relate to a computer-implemented method, wherein the measurement of the posterior portion of the eye of the subject includes a measure of tissue thickness.

In some aspects, the techniques described herein relate to a computer-implemented method, wherein the measurement of the posterior portion of the eye of the subject includes a measure of size.

In some aspects, the techniques described herein relate to a computer-implemented method, further including determining a diagnosis based on the measurement of the posterior portion of the eye of the subject.

In some aspects, the techniques described herein relate to a computer-implemented method, wherein the diagnosis includes myopia.

In some aspects, the techniques described herein relate to a computer-implemented method, wherein the diagnosis includes glaucoma.

In some aspects, the techniques described herein relate to a computer-implemented method, wherein the measurement of the posterior portion of the eye of the subject includes a degree of glaucoma progression.

In some aspects, the techniques described herein relate to a computer-implemented method, wherein the measurement of the posterior portion of the eye of the subject includes a biomechanical measurement.

In some aspects, the techniques described herein relate to a computer-implemented method, wherein the biomechanical measurement includes a measurement of mechanical strain.

In some aspects, the techniques described herein relate to a computer-implemented method, wherein the biomechanical measurement includes a measurement of stiffness.

In some aspects, the techniques described herein relate to a computer-implemented method, wherein at least one of the ultrasound data includes radiofrequency data.

In some aspects, the techniques described herein relate to a computer-implemented method, wherein determining, using OPE, the measurement of the posterior portion of the eye of the subject includes analyzing radiofrequency data.

In some aspects, the techniques described herein relate to a computer-implemented method, wherein determining, using OPE, the measurement of the posterior portion of the eye of the subject includes applying a speckle tracking algorithm to the ultrasound data.

In some aspects, the techniques described herein relate to a system including: an ultrasound probe; and a controller including at least one processor and at least one memory, the at least one memory having computer-executable instructions stored thereon that, when executed by the at least one processor, cause the at least one processor to: receive ultrasound data from the ultrasound probe; determine, using ocular pulse elastography (OPE), a measurement of a posterior portion of an eye of a subject based on the ultrasound data.

In some aspects, the techniques described herein relate to a system, wherein the at least one memory has further computer-executable instructions stored thereon that, when executed by the at least one processor, cause the at least one processor to control the ultrasound probe to generate a high-frequency ultrasound signal.

In some aspects, the techniques described herein relate to a method including: recording, using an ultrasound probe, ultrasound data from to a posterior portion of an eye of a subject; determining, using ocular pulse elastography (OPE), a measurement of the posterior portion of the eye of the subject based on the ultrasound data; and diagnosing an ocular disease based on the measurement of the posterior portion of the eye of the subject.

In some aspects, the techniques described herein relate to a method, further including treating the ocular disease.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for imaging eyes, it will become evident to those skilled in the art that the implementations are not limited thereto but are generally applicable for ultrasound imaging and measurement.

Described herein are systems and methods for ultrasound measurement of a posterior of the eye. The systems and methods described herein can be used for ocular pulse elastography. In an eye, the intraocular pressure (IOP) pulsates at every heartbeat as blood enters and drains from the choroid. This pulsation, called the ocular pulse, has an amplitude of approximately 3-4 mmHg in healthy eyes. This intrinsic cyclic loading can be exploited using an elastography method referred to herein as "ocular pulse elastography (OPE)." OPE can be based on the intrinsic ocular pulse and measurements of a tissue's reaction to the intrinsic ocular pulse. OPE can image the biomechanical responses of the cornea to the dynamic component of the IOP. OPE may not require external mechanical forces and thus improves the simplicity for clinical translation. Optionally, OPE can be combined with in-vivo measurement of the IOP profile using a dynamic contour tonometer (DCT) (e.g., the DCT sold under the trademark PASCAL by the Ziemer Group, Alton, IL, USA). This approach allows analyses of corneal biomechanical responses to patient-specific IOP.

Figure 1:
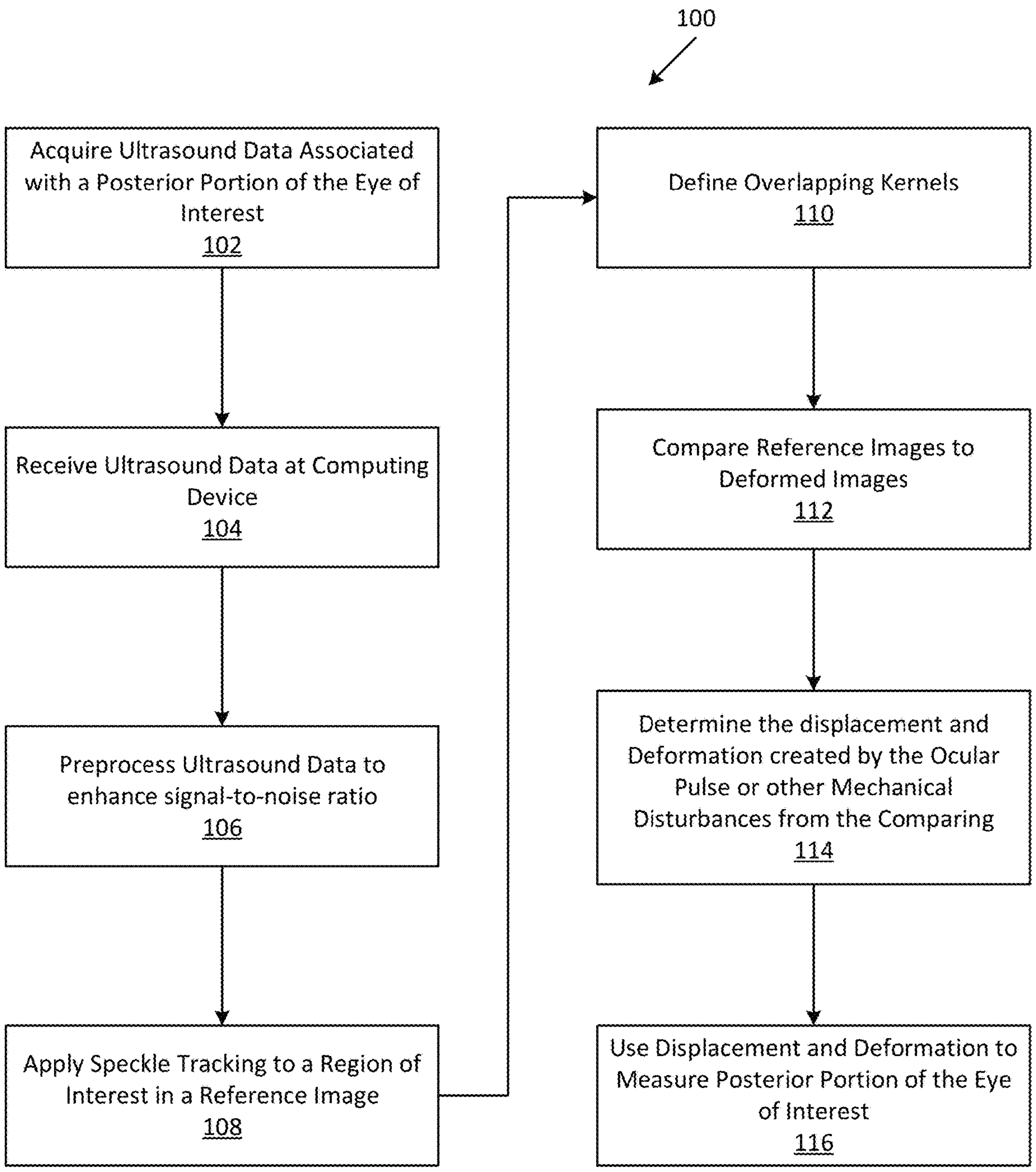
FIG. 1 illustrates a flow chart of an example method for measuring biophysical properties of an eye, according to implementations of the present disclosure.

With reference to FIG. 1, an example computer-implemented method 100 for measuring biophysical properties of an eye is shown.

At 102, ultrasound data of the eye is obtained. For example, the ultrasound data is maybe of the posterior of the eye. At 102, the data acquisition window is centered around the optic nerve head. To acquire the data, an ultrasound probe can be placed on the eye with the eyelids closed. Eye lubricating gel can be used to couple the transducer to tissue. The probe angle may be adjusted until a good view of the optic nerve and the peripapillary sclera is achieved. In some acquisitions, the probe can be held in place by a probe holder during image requisition. As a non-limiting example, the ultrasound data can be approximately 20 MHz ultrasound data. In some implementations, the ultrasound data includes an ultrasound cross section of the posterior portion of the eye. Alternatively or additionally, the at least one of the ultrasound data and the pulse elastography data can include radiofrequency data.

At 104, ultrasound data is received by a computing device. An example computing device is shown with respect to FIG. 4. As noted in 102 above, the ultrasound data may be high frequency ultrasound data.

Next processes to determine a measurement of a posterior portion of an eye of a subject based on the ultrasound data are performed. At 106, the ultrasound data is pre-processed to improve the signal-to-noise ratio prior to speckle tracking. This may be accomplished using algorithms such as temporal averaging and AI-based denoising. Next, at 108, ocular pulse elastography (OPE) may be used to determine the measurement using, e.g., an ultrasound speckle tracking algorithm optimized for 20 MHz ultrasound data. A region of interest is defined in a reference image. At 1110, within the region of interest, overlapping kernels are defined, each of which has a predetermined size (e.g., 31×21 pixels with 75% overlap).

At 112, the reference and deformed images (e.g., those due to a pulsation resulting from a heartbeat) are compared. For example, a cross-correlation based algorithm is used to find the new location of each kernel within a predefined search window in the neighborhood of the kernel, where the highest correlation coefficient is used as the new location of the kernel. Spline interpolation of the correlation coefficients is used to find the maximum correlation coefficient at sub-pixel resolution. The relative motion between the peripapillary sclera, the optic nerve head, the retrobulbar tissue, and any anterior tissue within the field of view is calculated for biomechanical analysis.

At 114, the displacement and deformation created by the ocular pulse or other mechanical disturbances is determined from the comparing. A least squares strain estimation technique is used to calculate the axial and lateral strains based on displacement gradients computed from the displacement field in the neighborhood of the kernel of interest. To reduce noise from unsatisfactory tracking, only kernels with a correlation coefficient greater than, e.g., 0.7 were used in the strain calculation. Strain maps are generated to provide a visualization of the spatial distribution of strain interpolated at each pixel. The average strain within the entire region of interest was also calculated.

At 116, using the displacement and deformation (strain) determinations, measurements of the region of interest of the posterior portion of the eye are determined. The measurement of the posterior portion of the eye can include a measurement of the posterior portion of the eye, and/or any portion of the posterior portion of the eye of the subject. As non-limiting examples, the measurement of the posterior portion of the eye of the subject can include a measure of size or tissue thickness. In some implementations the measurement of the posterior portion of the eye of the subject can be a degree of glaucoma progression. The use of ultrasound is real-time and more resistant to eye motion induced blur.

Implementations of the present disclosure can analyze radiofrequency data (e.g., when either the ultrasound or pulse elastography data includes radiofrequency data) to determine the measurement of the posterior portion of the eye of the subject.

Implementations of the present disclosure can optionally use a speckle tracking algorithm to determine a measurement of the posterior portion of the eye of the subject by applying the speckle tracking algorithm to the ultrasound data.

Alternatively or additionally, the measurement of the posterior portion of the eye of the subject at step 106 can be a biomechanical measurement. Non-limiting examples of biomechanical measurements include measurements of strain and stiffness.

In some implementations of the present disclosure, the computer-implemented method 100 can further include determining a diagnosis based on the measurement of the posterior portion of the eye of the subject determined at step 106. As additional non-limiting examples, if the subject is an eye, or part of an eye, the diagnosis can include myopia and/or glaucoma.

Implementations of the present disclosure further include methods. An example method includes recording, using an ultrasound probe, ultrasound data from a posterior portion of an eye of a subject, determining, using ocular pulse elastography (OPE), a measurement of the posterior portion of the eye of the subject based on the ultrasound data, and diagnosing an ocular disease based on the measurement of the posterior portion of the eye of the subject. In some implementations, the method can include treating the ocular disease.

Figure 4:
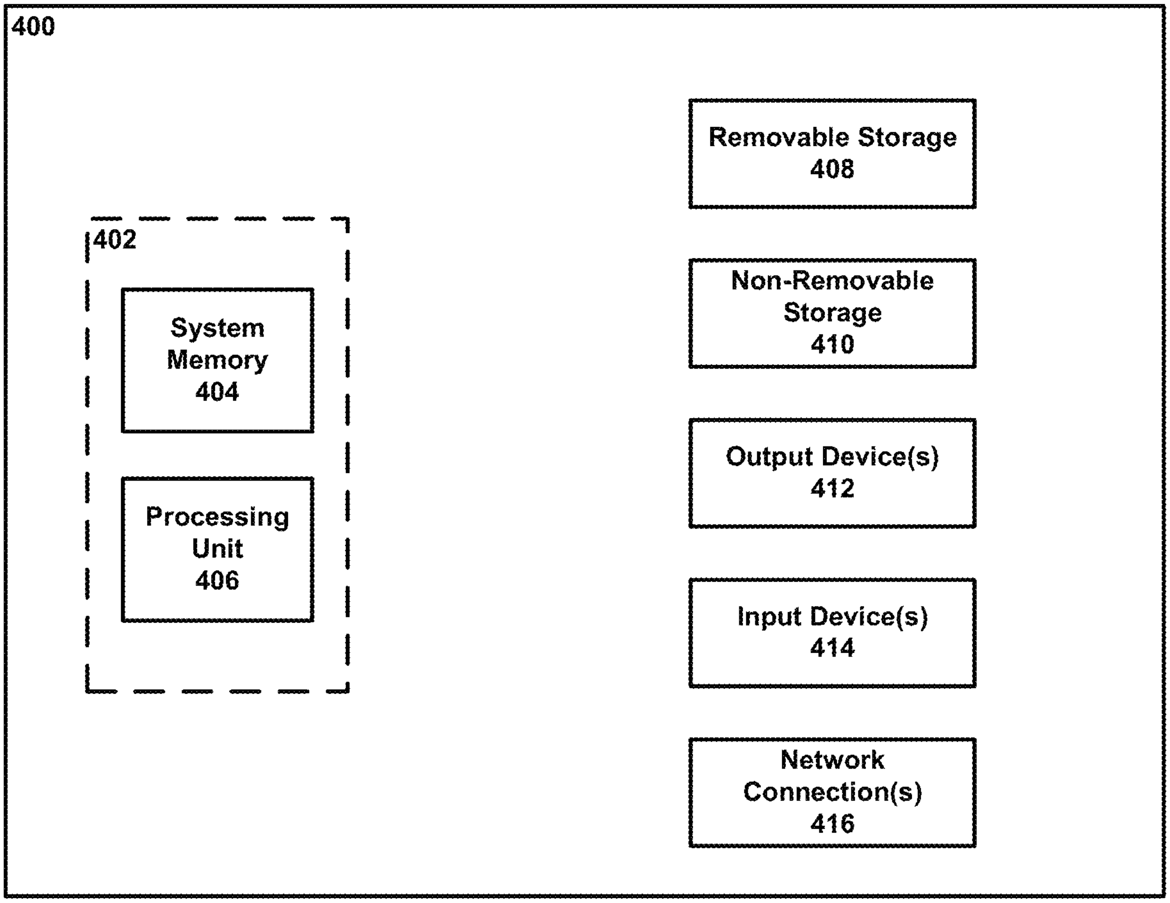
FIG. 4 is an example computing device.

Additionally, it should be understood that the methods described herein (including computer-implemented method 100 illustrated in FIG. 1) can be implemented as part of a system including an ultrasound probe and a controller (e.g., a controller including any/all of the components shown in the computing device of FIG. 4) where the controller is configured to perform the computer implemented methods described herein. The controller can also be configured to operate the ultrasound probe (for example, to control the ultrasound probe and cause the ultrasound probe to emit a high-frequency ultrasound signal).

Example

An example implementation of the present disclosure can use an ocular pulse elastography technique and ultrasound to measure the biomechanics of the tissue at the back of the eye, particularly including the peripapillary sclera (PPS) and the optic nerve head (ONH). Ultrasound can be safe and inexpensive. It also can have better penetration than light which cannot visualize the full thickness of PPS and ONH. The example implementation can record ultrasound data from a cross-section of the back of eye over several seconds, and then apply an ocular pulse elastography technique to extract information about the biomechanics of the PPS and ONH. The example implementation can optionally use 20 MHz ultrasound and analyze the radiofrequency data. The example implementation can obtain the anatomic measurements such as tissue thickness and size, as well as biomechanical measurements including strains and stiffness. Example applications include glaucoma and myopia diagnosis. An altered PPS biomechanics can indicate a higher risk for one or both diseases. The biophysical attributes can be used for clinical evaluation of a person's risk for glaucoma progression or risk for developing high myopia.

In vivo posterior eye imaging can be significant for glaucoma and myopia. In vivo imaging of the posterior sclera can be clinically useful. Optical coherence tomography (OCT) shows that the anterior peripapillary sclera (PPS) surface exhibits a v-shape that is more pronounced in glaucoma. PPS bowing can increase with age, a risk factor for glaucoma. Computational modeling has shown that sclera stiffness, radius, and thickness are among the top factors influencing intraocular pressure (IOP)-related stresses and strains in the optic nerve head (ONH), the primary site of damage in glaucoma. Conceptually, a thinner or weaker posterior sclera could be less supportive to the ONH, subjecting it to a greater risk for IOP-related damage. These predictions are supported by ex vivo experimental findings and are also consistent with the observation that high myopia (thinner and weaker sclera) is associated with an increased risk for glaucoma. Scleral biophysical attributes also play an important role in myopia. Animal models of form-deprivation myopia have consistently shown scleral thinning and remodeling at the onset and during the development of myopia. Implementations of the present disclosure include an effective imaging tool to characterize posterior sclera's biophysical attributes in vivo in the human eye. An effective in vivo imaging method to measure the biophysical attributes of the posterior eye can be used for clinical evaluation of a person's risk for glaucoma progression or risk for developing high myopia.

Besides the sclera, implementations described herein can also measure the optic nerve biophysical attributes, including its diameter and the spatial distribution of mechanical deformation in response to the ocular pulse. These parameters will be useful for evaluating a person's risk for glaucoma since the initial site of damage occurs in the optic nerve head.

Figure 2A:
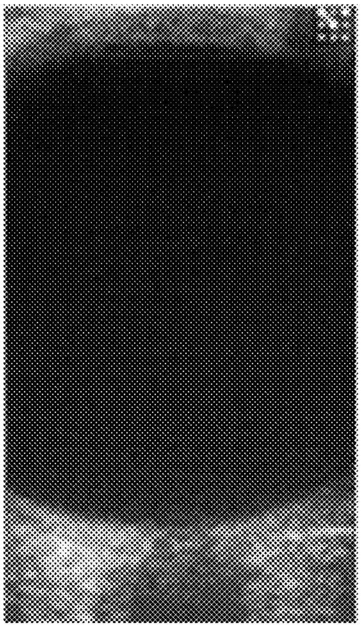
FIG. 2A illustrates an example ultrasound image scanned from the posterior eye of a volunteer, according to an example implementation of the present disclosure.
Figure 2B:
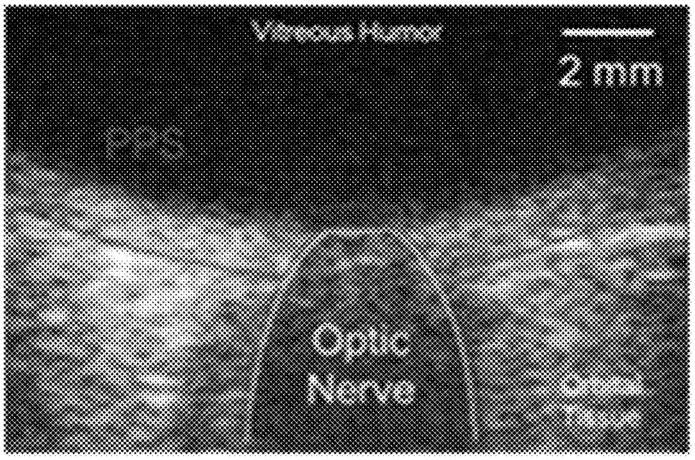
FIG. 2B illustrates an example ultrasound image scanned from the posterior eye of a volunteer, according to an example implementation of the present disclosure.
Figure 3:
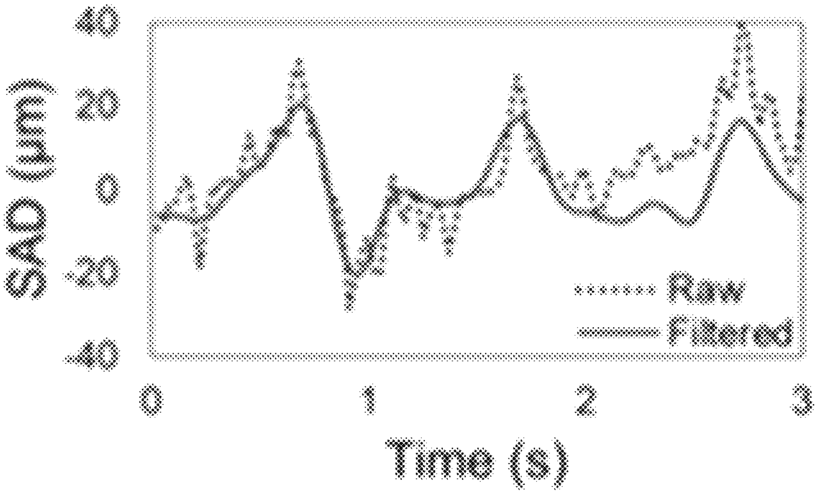
FIG. 3 illustrates an example of the sclera axial displacement (SAD) calculated using an example speckle tracking algorithm, according to an example implementation of the present disclosure.

FIG. 2A illustrates a first view of the eye obtained using an example implementation of the present disclosure, and FIG. 2B illustrates a second view of an eye obtained using the example implementation of the present disclosure. FIG. 3 illustrates an example of the sclera axial displacement (SAD) calculated using an example speckle tracking algorithm, according to an example implementation of the present disclosure.

It should be appreciated that the logical operations described herein with respect to the various figures may be implemented (1) as a sequence of computer implemented acts or program modules (i.e., software) running on a computing device (e.g., the computing device described in FIG. 4), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 4, an example computing device 400 upon which the methods described herein may be implemented is illustrated. It should be understood that the example computing device 400 is only one example of a suitable computing environment upon which the methods described herein may be implemented. Optionally, the computing device 400 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 400 typically includes at least one processing unit 406 and system memory 404. Depending on the exact configuration and type of computing device, system memory 404 may be volatile (such as random access memory (RAM)), non-volatile (such as read-only memory (ROM), flash memory, etc.), or some combination of the two. This most basic configuration is illustrated in FIG. 4 by dashed line 402. The processing unit 406 may be a standard programmable processor that performs arithmetic and logic operations necessary for operation of the computing device 400. The computing device 400 may also include a bus or other communication mechanism for communicating information among various components of the computing device 400.

Computing device 400 may have additional features/functionality. For example, computing device 400 may include additional storage such as removable storage 408 and non-removable storage 410 including, but not limited to, magnetic or optical disks or tapes. Computing device 400 may also contain network connection(s) 416 that allow the device to communicate with other devices. Computing device 400 may also have input device(s) 414 such as a keyboard, mouse, touch screen, etc. Output device(s) 412 such as a display, speakers, printer, etc. may also be included. The additional devices may be connected to the bus in order to facilitate communication of data among the components of the computing device 400. All these devices are well known in the art and need not be discussed at length here.

The processing unit 406 may be configured to execute program code encoded in tangible, computer-readable media. Tangible, computer-readable media refers to any media that is capable of providing data that causes the computing device 400 (i.e., a machine) to operate in a particular fashion. Various computer-readable media may be utilized to provide instructions to the processing unit 406 for execution. Example tangible, computer-readable media may include, but is not limited to, volatile media, non-volatile media, removable media and non-removable media implemented in any method or technology for storage of information such as computer readable instructions, data structures, program modules or other data. System memory 404, removable storage 408, and non-removable storage 410 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 406 may execute program code stored in the system memory 404. For example, the bus may carry data to the system memory 404, from which the processing unit 406 receives and executes instructions. The data received by the system memory 404 may optionally be stored on the removable storage 408 or the non-removable storage 410 before or after execution by the processing unit 406.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A computer-implemented method for measuring biophysical properties of a posterior portion of an eye, the computer-implemented method comprising:

receiving time-sequence ultrasound data of the posterior portion of the eye acquired by a 20 MHz ultrasound transducer while the eye is subjected only to intrinsic intraocular pressure variations and in the absence of externally applied mechanical forces;

preprocessing the ultrasound data to enhance signal-to-noise ratio to create pre-processed ultrasound data;

applying speckle tracking to a region of interest that includes peripapillary sclera and optic nerve head tissue in reference images within the time-sequence and defining overlapping kernels within the region of interest;

comparing the reference images with deformed images within the time-sequence in which the region of interest is displaced due to an intrinsic ocular pulse;

determining, from the comparing, the displacement and deformation within the region of interest based on relative motion between the reference images and the deformed images, including relative motion between the peripapillary sclera, the optic nerve head, and retrobulbar tissue; and using the displacement and deformation data from multiple cardiac cycles to measure the posterior portion of the eye, including at least one biophysical attribute selected from posterior scleral stiffness, posterior scleral strain, posterior scleral displacements, optic nerve head displacements, and optic nerve head strain, wherein the posterior portion of the eye includes structures behind the anterior hyaloid membrane of the eye.

2. The computer-implemented method of claim 1, wherein a data acquisition window associated with the ultrasound data is centered around an optic nerve head of the eye.

3. The computer-implemented method of claim 1, wherein the ultrasound data comprises a cross section image and associated radiofrequency data of the posterior portion of the eye.

4. The computer-implemented method of claim 1, wherein the measurement of the posterior portion of the eye of the subject comprises a measure of tissue thickness.

5. The computer-implemented method of claim 1, wherein the measurement of the posterior portion of the eye of the subject comprises anatomic measurements.

6. The computer-implemented method of claim 1, further comprising determining a diagnosis based on the measurement of the posterior portion of the eye of the subject.

7. The computer-implemented method of claim 6, wherein the diagnosis comprises myopia.

8. The computer-implemented method of claim 6, wherein the diagnosis comprises a degree of myopia progression.

9. The computer-implemented method of claim 6, wherein the diagnosis comprises glaucoma.

10. The computer-implemented method of claim 1, wherein the measurement of the posterior portion of the eye of the subject comprises a degree of glaucoma progression.

11. The computer-implemented method of claim 1, wherein the measurement of the posterior portion of the eye of the subject comprises a biomechanical measurement.

12. The computer-implemented method of claim 11, wherein the biomechanical measurement comprises a measurement of strain.

13. The computer-implemented method of claim 11, wherein the biomechanical measurement comprises a measurement of stiffness.

14. The computer-implemented method of claim 1, wherein at least one of the ultrasound data comprises radiofrequency data.

15. The computer-implemented method of claim 14, wherein determining, using ocular pulse elastography (OPE), the measurement of the posterior portion of the eye of the subject comprises analyzing radiofrequency data.

16. The computer-implemented method of claim 1, wherein the speckle tracking algorithm is optimized to a frequency of the ultrasound data.

17. A system comprising an ultrasound probe having a 20 MHz transducer and a controller comprising at least one processor and at least one memory, the at least one memory having computer-executable instructions stored thereon that, when executed by the at least one processor, cause the at least one processor to:

receive ultrasound data from the ultrasound probe, the ultrasound data being time-sequence ultrasound data of a posterior portion of an eye that includes structures behind the anterior hyaloid membrane of the eye acquired while the eye is subjected only to intrinsic intraocular pressure variations and in the absence of externally applied mechanical forces;

preprocess the ultrasound data to enhance signal-to-noise ratio to create pre-processed ultrasound data;

apply speckle tracking to a region of interest that includes peripapillary sclera and optic nerve head tissue in reference images within the time-sequence and defining overlapping kernels within the region of interest;

compare the reference images with deformed images within the time-sequence in which the region of interest is displaced due to an intrinsic ocular pulse;

determine, from the comparing, a displacement and deformation within the region of interest based on relative motion between the reference images and the deformed images, including relative motion between the peripapillary sclera, the optic nerve head, and retrobulbar tissue, induced by an intrinsic ocular pulse of the eye; and use the displacement and deformation from multiple cardiac cycles to measure the posterior portion of the eye by computing at least one biophysical attribute selected from posterior scleral stiffness, posterior scleral strain, posterior scleral displacements, optic nerve head displacements, and optic nerve head strain.

18. The system of claim 17, wherein the at least one memory has further computer-executable instructions stored thereon that, when executed by the at least one processor, cause the at least one processor to control the ultrasound probe to generate a high-frequency ultrasound signal.

19. A method comprising:

recording, using an ultrasound probe having a 20 MHz transducer, ultrasound data from a posterior portion of an eye of a subject, wherein the posterior portion of the eye includes structures behind the anterior hyaloid membrane of the eye, the ultrasound data being recorded as time-sequence ultrasound data while the eye is subjected only to intrinsic intraocular pressure variations and in the absence of externally applied mechanical forces;

preprocessing the ultrasound data to enhance signal-to-noise ratio to create pre-processed ultrasound data;

applying speckle tracking to a region of interest that includes peripapillary sclera and optic nerve head tissue in reference images within the time-sequence and defining overlapping kernels within the region of interest;

comparing the reference images with deformed images within the time-sequence in which the region of interest is displaced due to an intrinsic ocular pulse;

determining, from the comparing, the displacement and deformation created by an ocular pulse within the region of interest, including relative motion between peripapillary sclera, optic nerve head, and retrobulbar tissue;

using the displacement and deformation from multiple cardiac cycles to measure the posterior portion of the eye by computing at least one biophysical attribute selected from posterior scleral stiffness, posterior scleral strain, posterior scleral displacement, optic nerve head displacement, and optic nerve head strain; and diagnosing an ocular disease based on the measurement of the posterior portion of the eye of the subject.

20. The method of claim 19, further comprising treating the ocular disease.

* * * * *